(12) United States Patent
Osorio

(10) Patent No.: US 11,026,623 B2
(45) Date of Patent: *Jun. 8, 2021

(54) SEIZURE DETECTION BASED ON WORK LEVEL EXCURSION

(71) Applicant: Flint Hills Scientific, L.L.C., Lawrence, KS (US)

(72) Inventor: Ivan Osorio, Leawood, KS (US)

(73) Assignee: Flint Hills Scientific, L.L.C., Lawrence, KS (US)

( * ) Notice: Subject to any disclaimer, the term of this patent is extended or adjusted under 35 U.S.C. 154(b) by 545 days.

This patent is subject to a terminal disclaimer.

(21) Appl. No.: 15/726,683

(22) Filed: Oct. 6, 2017

(65) Prior Publication Data

US 2018/0028105 A1    Feb. 1, 2018

Related U.S. Application Data

(63) Continuation of application No. 14/169,006, filed on Jan. 30, 2014, now Pat. No. 9,788,779, which is a continuation-in-part of application No. 14/084,513, filed on Nov. 19, 2013.

(60) Provisional application No. 61/801,950, filed on Mar. 15, 2013, provisional application No. 61/798,274, filed on Mar. 15, 2013, provisional application No. 61/793,292, filed on Mar. 15, 2013, provisional application No. 61/794,540, filed on Mar. 15, 2013, provisional application No. 61/785,429, filed on Mar. 14, 2013.

(51) Int. Cl.
*A61B 5/00* (2006.01)
*A61B 5/11* (2006.01)
*A61B 5/0205* (2006.01)
*A61B 5/145* (2006.01)
*A61B 5/024* (2006.01)
*A61B 5/08* (2006.01)
*A61B 5/1455* (2006.01)

(52) U.S. Cl.
CPC .......... *A61B 5/4094* (2013.01); *A61B 5/1118* (2013.01); *A61B 5/4866* (2013.01); *A61B 5/024* (2013.01); *A61B 5/0205* (2013.01); *A61B 5/0816* (2013.01); *A61B 5/14539* (2013.01); *A61B 5/14551* (2013.01); *A61B 5/4848* (2013.01)

(58) Field of Classification Search
CPC ... A61B 5/1118; A61B 5/4866; A61B 5/4094; A61B 5/024; A61B 5/0816; A61B 5/14539; A61B 5/0205; A61B 5/14551; A61B 5/4848
See application file for complete search history.

(56) References Cited

U.S. PATENT DOCUMENTS 8,209,018 B2 *  6/2012  Osorio ................ A61B 5/4094
                                                  607/45

* cited by examiner

*Primary Examiner* — Mark Bockelman
(74) *Attorney, Agent, or Firm* — CF3; Stephen Eisenmann

(57) ABSTRACT

We report a method of determining an occurrence of an epileptic convulsive seizure in a patient, comprising: receiving body data from a patient during a first time period, determining a work level relating to said first time period at least based partially upon said body data; determining whether said work level exceeds an extreme work level threshold; performing a responsive action, in response to a determination that said work level exceeds said extreme work level threshold. We also report a medical device system configured to implement the method. We also report a non-transitory computer readable program storage unit encoded with instructions that, when executed by a computer, perform the method.

20 Claims, 10 Drawing Sheets

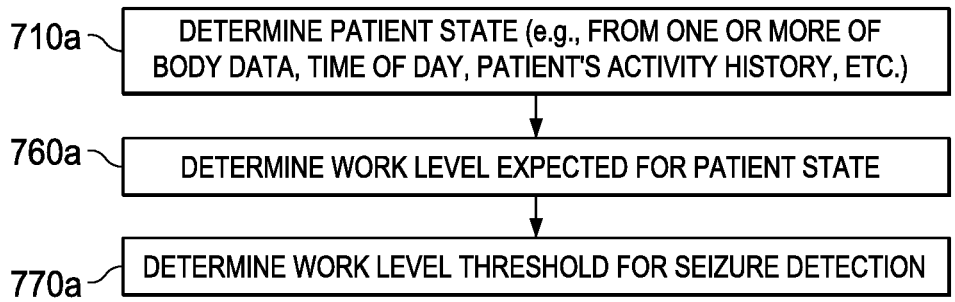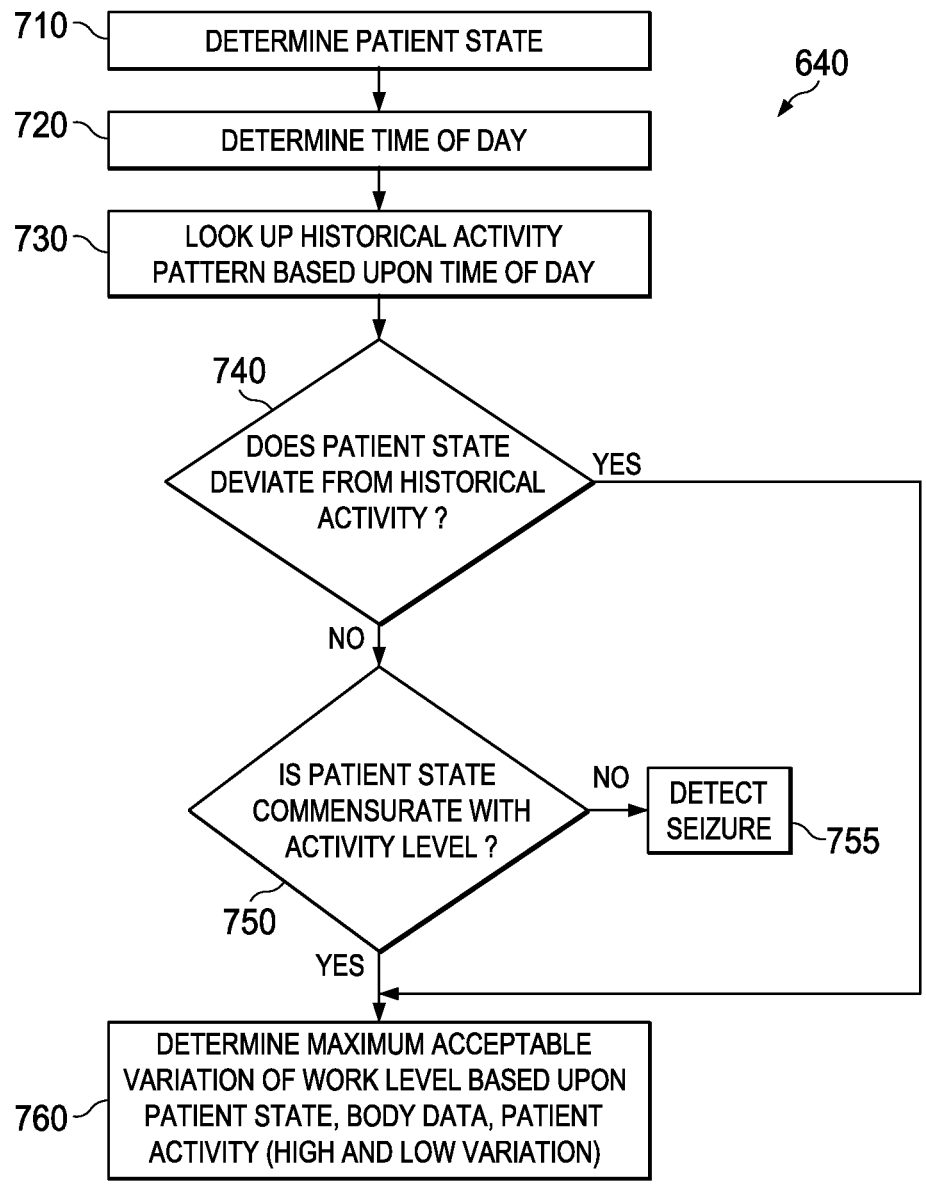

SEIZURE DETECTION BASED ON WORK LEVEL EXCURSION

CROSS-REFERENCE TO RELATED APPLICATIONS

The present application claims priority to and is a continuation of U.S. patent application Ser. No. 14/169,006, entitled "Seizure Detection Based on Work Level Excursion" which was filed on Jan. 30, 2014, which claimed priority to and is a continuation-in-part of U.S. patent application Ser. No. 14/084,513, entitled "Pathological State Detection Using Dynamically Determined Body Index Range Values" which was filed on Nov. 19, 2013. Further, U.S. patent application Ser. No. 14/169,006 claims priority to and the benefit of prior-filed provisional applications 61/785,429, filed on Mar. 14, 2013; and 61/798,274, 61/793, 292, 61/794,540, and 61/801,950, all filed on Mar. 15, 2013, all of above-referenced disclosures are hereby incorporated by reference.

FIELD OF THE INVENTION

This disclosure relates to medical device systems and methods capable of detecting epileptic seizures.

SUMMARY OF THE INVENTION

In some embodiments, the present disclosure relates to a method of determining an occurrence of an epileptic convulsive seizure in a patient, comprising: receiving body data from a patient during a first time period, determining a work level relating to said first time period at least based partially upon said body data; determining whether said work level exceeds an extreme work level threshold; performing a responsive action, in response to a determination that said work level exceeds said extreme work level threshold, wherein said responsive action is selected from: determining said occurrence of said convulsive seizure, or implementing a confirmation test to confirm said occurrence of said epileptic convulsive seizure. In some embodiments, the present disclosure relates to a method of determining an occurrence of an epileptic seizure in a patient, comprising receiving body data from a patient during a first time period, determining a work level relating to said first time period at least based partially upon said body data; determining an activity level of said patient during said first time period; determining whether said work level is incommensurate with said activity level; and determining said occurrence of said epileptic seizure, based at least in part on said incommensurateness of said work level with said activity level.

In other embodiments, the present disclosure relates to a medical device system, comprising at least one sensor, each configured to collect at least one body signal from a patient relating to a work level of said patient; and a medical device, comprising: a body data module configured to receive body data; a patient state data unit configured to determine the patient state based upon said body data; a work level data module configured to determine a patient's first work level during a first time period, and the patient's second work level during a second time period; a work level excursion module configured to determine a work level excursion threshold based at least one said body data, time of day, or said patient state; a work level excursion test module configured to determine whether said second work level exceeds said first work level by greater than an amount of said first work level excursion threshold; and a controller to perform at least one of warning of a pathological state, providing a therapy, or logging said occurrence of said pathological state.

In some embodiments, the present disclosure relates to a method of determining a work level of a subject's brain, comprising: determining a first oxygen saturation, concentration, or pressure of the subject's blood at a first location in an artery; determining a second oxygen saturation, concentration, or pressure of the subject's blood at a second location in a vein or venous sinus; and determining the work level of the subject's brain based on said first oxygen saturation, concentration, or pressure and said second oxygen saturation, concentration, or pressure.

In other embodiments, the present disclosure relates to a medical device system, comprising: a first sensor configured to collect first oxygen saturation, concentration, or pressure data of a subject's blood from a first location in an arterial vessel; a second sensor configured to collect second oxygen saturation, concentration, or pressure data of the subject's blood from a second location in a venous structure; and a medical device, comprising: a first location oxygen saturation, concentration, or pressure module configured to determine a first oxygen saturation, concentration, or pressure from said first oxygen saturation, concentration, or pressure data; a second location oxygen saturation, concentration, or pressure module configured to determine a second oxygen saturation, concentration, or pressure from said second oxygen saturation data; an oxygen saturation, concentration, or pressure difference module configured to determine a difference between the first oxygen saturation, concentration, or pressure and the second oxygen saturation; and a brain work level determination module configured to determine a work level of the subject's brain based on the difference.

In some embodiments, the present disclosure relates to a method of determining a work level of a subject's body, comprising: determining a first oxygen saturation, concentration, or pressure of the subject's arterial blood at a first location selected from one of a left ventricle, an aorta, a branch of the aorta, or a sub-branch of the aorta; determining a second oxygen saturation, concentration, or pressure of the subject's venous blood at a second location in a blood vessel selected from one of a superior vena cava, an inferior vena cava, a right ventricle, a pulmonary artery, or a jugular vein; and determining the work level of the subject's body or body parts based on the difference.

In other embodiments, the present disclosure relates to a medical device system, comprising: a first sensor configured to collect first oxygen saturation, concentration, or pressure data of the subject's arterial blood from a first location selected from a left ventricle, an aorta, a branch of the aorta, or a sub-branch of the aorta; a second sensor configured to collect second oxygen saturation, concentration, or pressure data of a subject's venous blood from a second location in a blood vessel selected from a superior vena cava, an inferior vena cava, a right ventricle, a pulmonary artery, or a jugular vein; and a medical device, comprising: a first location oxygen saturation, concentration, or pressure module configured to determine a first oxygen saturation, concentration, or pressure from said first oxygen saturation, concentration, or pressure data; a second location oxygen saturation, concentration, or pressure module configured to determine a second oxygen saturation, concentration, or pressure from said second oxygen saturation, concentration, or pressure data; and a body or body parts work level determination module configured to determine a work level of the subject's body or body parts based on the first oxygen saturation, concentration, or pressure and the second oxygen saturation, concentration, or pressure.

In some embodiments, the present disclosure relates to a non-transitory computer readable program storage unit encoded with instructions that, when executed by a computer, perform a method as described above.

DESCRIPTION OF THE DRAWINGS

The disclosure may be understood by reference to the following description taken in conjunction with the accompanying drawings, in which like reference numerals identify like elements, and in which:

FIG. 7A shows a flowchart depiction of some steps of the method of FIG. 7, according to some embodiments of the present disclosure;

FIG. 7B shows a flowchart depiction of some steps of the method of FIG. 7, according to some embodiments of the present disclosure;

Figure 1:
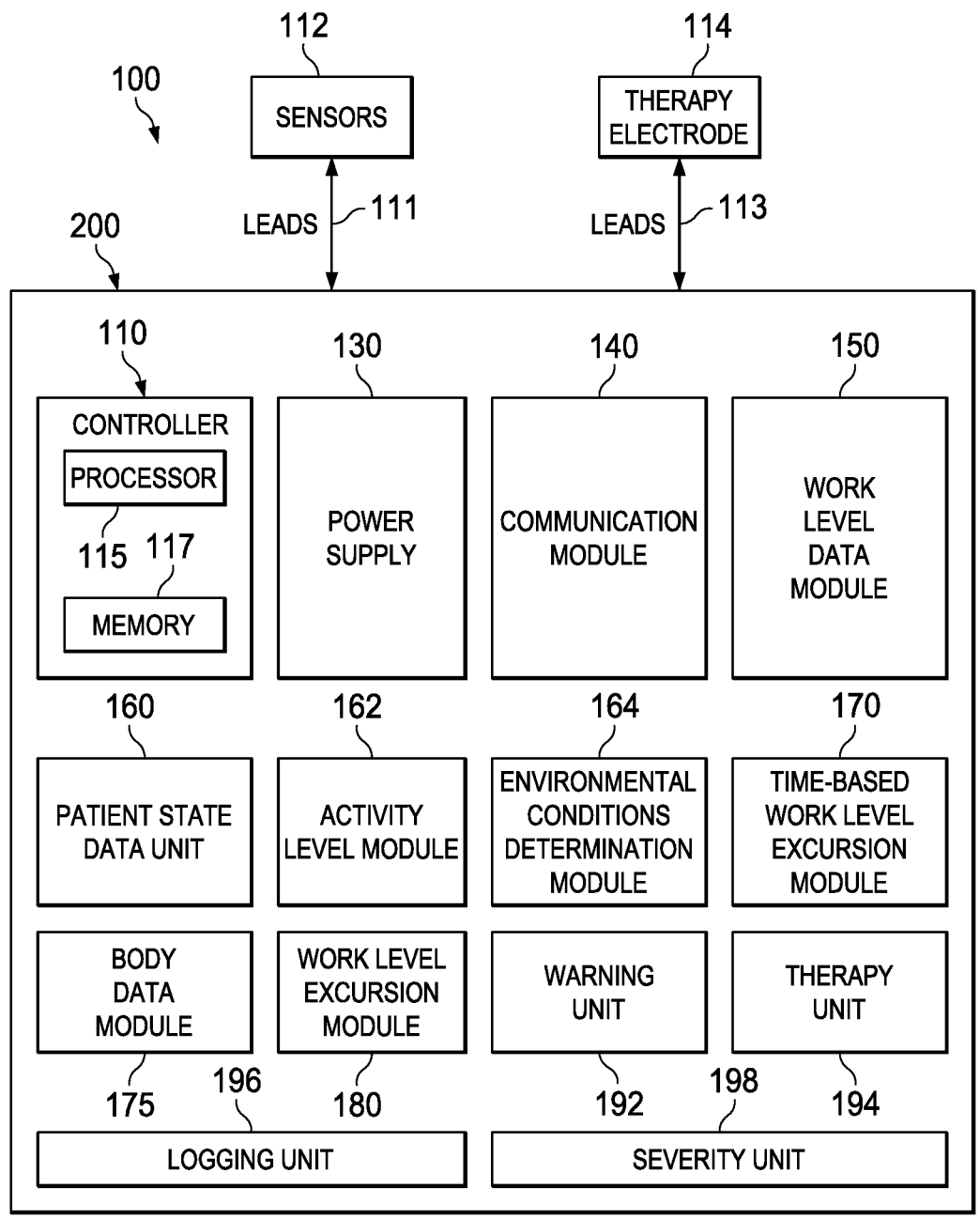
FIG. 1 shows a schematic diagram of a medical device system, in accordance with some embodiments of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

Some embodiments disclosed herein provide for performing a convulsive seizure detection based upon a work level of a patient. Body signal(s) from a patient, such as arteriovenous differences in oxygen, may be acquired during a first time period. Based at least partially upon the body signal(s), a work level of the patient for the first time period is determined. A determination can then be made as to whether the work level exceeds an extreme work level threshold or some other non-extreme reference level value. If the work level exceeds an extreme threshold, a determination that a convulsive seizure has occurred may be made. Further, a confirmation test to confirm the convulsive seizure may be performed.

"Work level" herein refers to the energy consumption of the patient's body or a part thereof (e.g., the brain). Energy consumption may, in some embodiments, be measured by differences in oxygen saturation, concentration, or pressure between arterial and venous locations. In some embodiments of this disclosure, work level may be determined using measures of kinetic activity (force, amplitude, velocity, direction, and duration and rate of muscle contractions) or autonomic activity such as heart rate. "Work level" in this disclosure does not refer exclusively to the patient's physical activity. Physical activity may be only one of multiple physiological events or states leading to energy consumption by the patient's body or a part thereof. "Work level" may also refer to the physics definition, $W = F \times d$. The application of force over distance may be only one of multiple actions by a patient leading to energy consumption by the patient's body or a part thereof.

One of the meanings of extreme work level herein is a work level that cannot be accomplished volitionally. Extreme work levels may exceed the maximal volitional work level that may be performed by the patient per unit time, and/or may exceed the total duration of a work that could be sustained volitionally by a patient. Convulsive (generalized tonic or clonic or tonic-clonic) seizures are associated with a work level (determined using metabolic, kinetic or other signals) that is extreme.

Figure 10A:
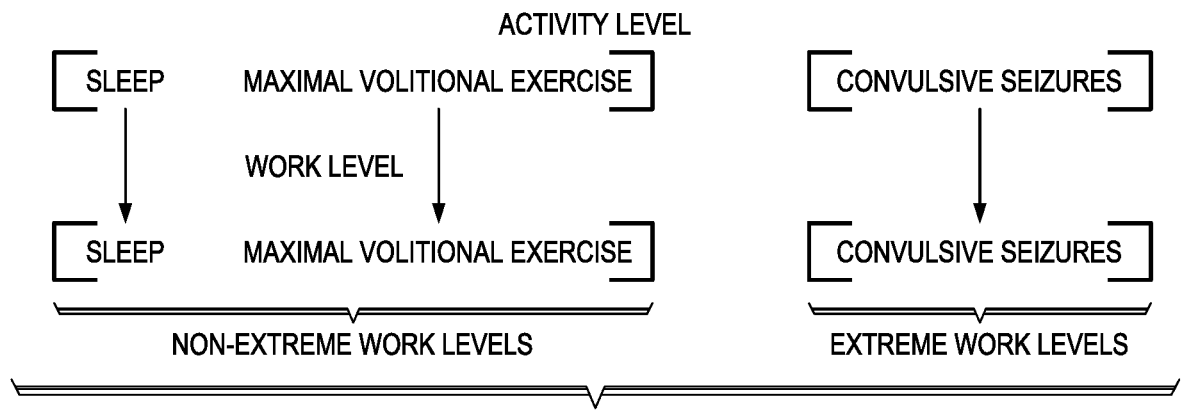
FIG. 10A qualitatively shows the typical correspondence between activity level and work level for convulsive seizures, according to some embodiments of the present disclosure.

FIG. 10A illustrates, in qualitative fashion, typical correspondence or commensurateness between ranges (minimum to maximum) of activity and work levels for non-seizure conditions, e.g., from sleep up to maximal volitional exercise. It further illustrates that while the activity and work levels for convulsive seizures are much greater than for non-seizures, these levels are still commensurate.

Figure 10B:
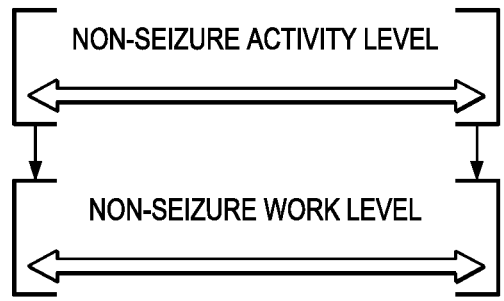
FIG. 10B qualitatively shows a typical correspondence between non-seizure activity level and non-seizure work level, according to some embodiments of the present disclosure.

FIG. 10B illustrates, in qualitative fashion, typical commensurateness between activity and work levels for non-seizure or interictal periods for a typical patient.

Figure 10C:
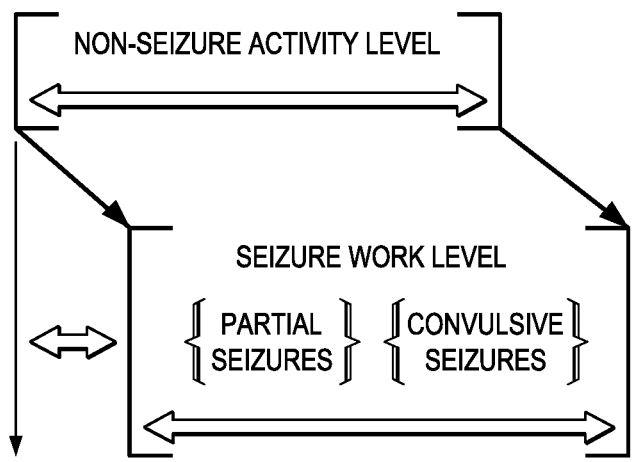
FIG. 10C qualitatively shows a typical lack of correspondence between non-seizure activity level and seizure work level, for both partial and convulsive seizures, according to some embodiments of the present disclosure.

FIG. 10C depicts, in qualitative fashion, typical differences between non-seizure activity level and seizure work level. Notice that while the work level for partial seizures is generally within the non-seizure activity level range, it is incommensurate with the current (e.g., at the time(s) the change in work level occurs) non-seizure activity level. The work level of epileptic convulsive seizures is well above the non-seizure activity level range. On the other hand, the work level of generalized atonic seizures and partial seizures manifesting with motionlessness or with bradycardia may be below the non-seizure activity range and/or incommensurate with the current non-seizure activity level. Thus, "incommensurateness" as used herein may be observable by a work level outside an expected work level range, above an upper work level threshold, and/or below a lower work level threshold.

In another embodiment of the present disclosure, a pathological state of a patient may be detected based upon an excursion of a work level of the patient. The excursion may relate to an increase in a work level during a second time period compared to a work level during a first time period. Body signal(s) from a patient may be acquired during a first time period. Based at least partially upon the body signal(s), a first work level of the patient for the first time period is determined. Body signal(s) from a patient may be acquired during a second time period. Based at least partially upon the body signal(s), a second work level of the patient for the second time period is determined. The first and second work levels are compared and a determination is made whether the second work level exceeds the first work level by a work level excursion threshold.

In one embodiment, if the second work level exceeds the first work level by a certain quantity that may be set as a threshold, a pathological state may be deemed to have occurred. In general, a threshold may be set in a relative or absolute manner dependent upon the context and clinical application of the situation. In another embodiment, if the second work level does not exceed the first work level but said work level is incommensurate with the on-going activity levels (e.g., too high or too low a work level relative to a work level expected for the patient's activity level), a pathological state may be deemed to have occurred.

In response to detecting the pathological state, a responsive action may be taken, wherein the responsive action may include providing a warning (e.g., locally (at the site where the patient is located at the time of the convulsion) and/or remotely (to an EMT, a doctor's office, a nurse's station, etc.), providing a therapy, and/or logging the occurrence of the pathological event and its characteristic (e.g., severity, prevailing conditions at date/time of occurrence, etc.). The environmental factors surrounding the occurrence of the pathological event may also be logged and taken into account into the determination of the pathological event. In an alternative embodiment, the above analyses may be performed by using a moving window to acquire body data signals. In one embodiment, the work level excursion threshold may be determined based upon at least one of the body signal acquired during the first time period or the work level during the first time period.

Determination of the value of the extreme work level threshold would allow classification of seizures into convulsive and non-convulsive (e.g. partial): Work levels that reach or exceed the extreme threshold correspond to convulsions (e.g., generalized tonic, tonic-clonic, clonic-tonic-clonic or myoclonic) and those associated with work levels that are incommensurate with corresponding activity levels but remain below the extreme threshold, correspond to partial seizures. That is, work level excursions or degree of incommensurateness between activity level and work level may be used in one or more embodiments in this disclosure, to detect and quantify seizures and to classify them as epileptic or non-epileptic (in the case of convulsive seizures) and the epileptic seizures as convulsive or non-convulsive (e.g., partial). Moreover, these two observables may be used to distinguish inter-ictal from the ictal and post-ictal states.

FIG. 1 shows a schematic representation of a medical device system, according to some embodiments of the present disclosure. The medical device system 100 may comprise a medical device 200, body data sensor(s) 112, and lead(s) 111 coupling the sensor(s) 112 to the medical device 200. In one embodiment, body data sensor(s) 112 may each be configured to collect data from a patient relating to a time series of body data values. In one embodiment, the body data may be selected from heart rate, blood pressure, respiratory rate, dermal activity, oxygen saturation, or end-tidal $CO_2$ among others.

"Oxygen saturation" is used herein to encompass measures of oxygen in the patient's blood. Such measures include $O_2$ concentration and $O_2$ partial pressure, among others. In yet other embodiments, glucose or ATP consumption or production of certain byproducts of metabolism, such as $CO_2$ or lactic acid, may be used to determine work level in the brain, other body parts (e.g., muscles), or the body as a whole.

Various components of the medical device 200, such as controller 110, processor 115, memory 117, power supply 130, communication module 140, warning unit 192, therapy unit 194, logging unit 196, and severity unit 198 have been described in other patent applications assigned to Flint Hills Scientific, LLC or Cyberonics, Inc., such as, U.S. Ser. No. 12/896,525, filed Oct. 1, 2010; U.S. Ser. No. 13/288,886, filed Nov. 3, 2011; U.S. Ser. No. 13/449,166, filed Apr. 17, 2012; and U.S. Ser. No. 13/678,339, filed Nov. 15, 2012. Each of the patent applications identified in this paragraph is hereby incorporated herein by reference.

The medical device 200 may comprise at least one therapy delivery source (e.g., electrode or catheter) 114, configured to deliver an electrical stimulation or some other form of therapy (e.g., a drug) to a tissue of the patient, such as a neural tissue of the patient. An exemplary electrical stimulation therapy is vagus nerve stimulation therapy, such as that provided by implantable VNS devices commercially available from Cyberonics, Inc. Alternatively or in addition, pharmacological, thermal, or other therapies may be used in this disclosure.

The medical device 200 may comprise a body data module 175 configured to receive body data from the at least one sensor(s) 112.

The medical device 200 may comprise a patient's state data unit 160 configured to determine a patient's state based upon one or more of the body data, the time of day, or an activity level history of the patient, among others. A patient's state may be selected from one or more of asleep or awake, resting or active, etc.

The medical device 200 may comprise an activity level module 162 configured to determine the patient's activity level based at least in part on one or more of the body data, the time of day, or an activity level history of the patient. The patient activity level differs from patient state by being more short-term in focus and more immediately (in the temporal sense) derived from its inputs. For example, a patient in the awake state may be motionless or active ranging from slow walking to vigorous exercise. These activity levels may change within seconds/instantaneously and their determination is far more susceptible to rapid changes than is the case for a patient that may be continuously in an awake state for 12-16 hours per day. That said, there may occur circumstances wherein the patient activity level and the patient state provide nearly the same information, e.g., when the patient is asleep.

The medical device 200 may comprise and environmental conditions determination module 164 configured to determine one or more environmental conditions (e.g., time of day, ambient temperature, altitude, ambient humidity, barometric pressure, luminance, etc.). One or more of the determined environmental conditions may be provided to other component(s) of the medical device 200, e.g., the patient state data unit 160, the activity level module 162, etc., to allow determinations of patient state, activity level, etc. to be based at least in part on the one or more determined environmental conditions.

The medical device 200 may comprise a work level data module 150 configured to determine a patient's work level. For example, the work level data module 150 may be configured to determine a first work level of the patient during a first time period, and the patient's second work level during a second time period.

The medical device 200 may comprise a time-based work level excursion module 170 configured to determine a work level expected for a patient at a given time of day, week, month, season, or year. In some embodiments, the time-based work level excursion module 170 may determine the work level expected for a patient based at least in part on at least one of body data or patient state, in addition to time of day, etc.

The medical device 200 may comprise a work level excursion module 180 configured to determine whether a work level is undergoing a work level excursion indicative of a seizure. For example, the work level excursion module 180 may determine if a work level exceeds an extreme work level threshold. In some embodiments, the work level excursion module 180 may determine an extreme work level threshold, such as at a value of three standard deviations above the patient's mean or median work level. This mean may be determined over any time scale (e.g., 1-10 sec.; 11 sec-1 hr; up to 24 hr or more than 24 hr), up to all available data for the patient. In some embodiments, the extreme work level threshold may be set at an elevated level (e.g., more than three standard deviations) or at a lowered level (e.g., less than three standard deviations) from a particular body data state for the patient, such as moderate or strenuous exercise. Other statistical markers (e.g., percentiles) may be used instead of, or in addition to, the mean or median.

For another example, in some embodiments, the work level excursion module 180 may determine the work level expected for a patient based on at least one of body data, time of day, or patient state. In light of a determined expected work level, the work level excursion module 180 may determine if a second work level exceeds a first work level by greater than an amount of a first work level excursion threshold. The first work level excursion threshold may be pre-specified and fixed, or adaptive or variable based on factors such as those given elsewhere. For yet another example, the work level excursion module 180 may determine if an observed work level is incommensurate with the patient's activity level. The patient's activity level may be determined by activity level module 162 described above.

A work level excursion relative to a first work level excursion threshold and/or a range expected for a patient's activity level may be considered an indication of a pathological state, such as a partial epileptic seizure, or a convulsive epileptic seizure.

An extreme work level excursion (beyond an extreme work level threshold) may be considered an indication of a convulsive epileptic seizure.

If a seizure is indicated by a work level excursion, in one embodiment, the controller 110 may be configured to perform at least one responsive action, in response to a determination that said work level excursion is indicative of a seizure, wherein said responsive action is selected from determining said occurrence of said seizure, or implementing a confirmation test to confirm said occurrence of said seizure.

Figure 2:
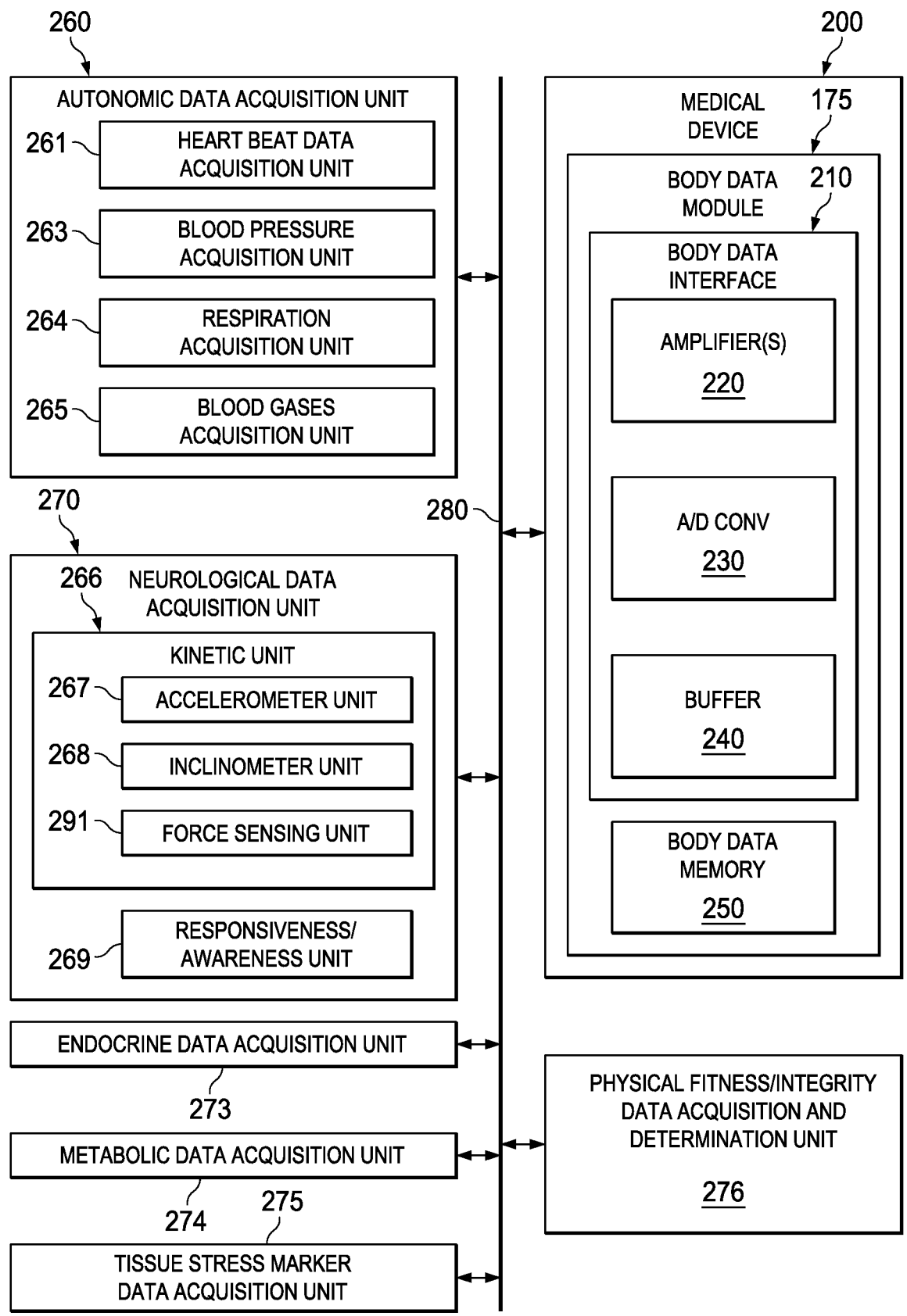
FIG. 2 shows a schematic diagram of portions of a medical device system, in accordance with some embodiments of the present disclosure.

FIG. 2 shows a schematic representation of components of the medical device system, particularly, body data module 175 of medical device 200, as well as an autonomic data acquisition unit 260, a neurological data acquisition unit 270, an endocrine data acquisition unit 273, a metabolic data acquisition unit 274, a tissue stress marker data acquisition unit 275, and a physical fitness/integrity data acquisition unit 276. In other, non-depicted embodiments, the medical device system may comprise none, one, or some of the data acquisition units 260-276. More information regarding multiple body data types, data collection thereof, and use thereof in epileptic event detection may be found in other patent applications assigned to Flint Hills Scientific, LLC or Cyberonics, Inc., such as, U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

Of interest in FIG. 2 is force sensing unit 291 configured to determine an amount of force generated by part or all of a patient's body.

Also of interest in FIG. 2 is blood gases acquisition unit 265. In some embodiments, blood gases acquisition unit 265 may be configured to detect blood oxygen saturation, concentration, or pressure at one or more points in a patient's vasculature, (e.g., carotid artery, jugular vein, superior vena cava, inferior vena cava, a left ventricle of the heart, right ventricle of the heart, aorta, branch of the aorta, or a sub-branch of the aorta, among others). In alternative embodiments, blood gases acquisition unit 265 may be configured to detect blood oxygen saturation, concentration, or pressure in other blood vessels and/or organ target sites of the patient's body. In some embodiments, blood gases unit 265 may comprise an arterio-venous oxygen difference determination unit 2741 configured to determine an arterio-venous oxygen difference, and an oxygen consumption determination unit 2742 configured to determine an oxygen consumption from the arterio-venous oxygen difference. In yet other embodiments, $CO_2$ pressures or concentrations may be measured at one or more body locations.

Figure 3:
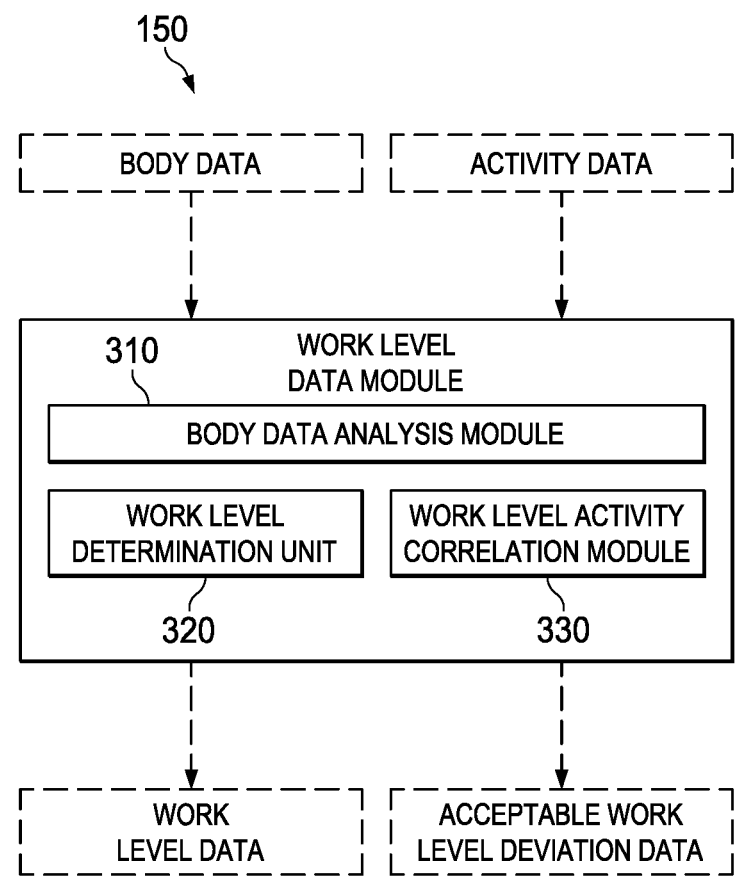
FIG. 3 shows a schematic diagram of a work level data module, according to some embodiments of the present disclosure.

FIG. 3 shows a work level data module 150 (e.g., such as that in FIG. 1) in more detail. The work level data module 150 may receive one or both of body data and activity data from the patient.

The work level data module 150 may comprise a body data analysis module 310 configured to analyze received body data for use by other components of the work level data module 150 or other modules or units of medical device 200.

The work level data module 150 may comprise a work level determination unit 320 configured to determine a work level of a patient from one or more of the received body data or the received activity data. In one embodiment, the work level determination unit 320 may be configured to determine a work level of a patient from body data related to oxygen consumption. Alternatively or in addition, the work level determination unit 320 may be configured to determine a work level of a patient from data related to kinetic activity, cognitive activity, emotional activity, or other patient activity.

The work level data module 150 may comprise a work level-activity correlation module 330 configured to determine a correlation between the work level determined by work level determination unit 320 and certain received body signals data. This correlation may be useful as a check on the determination of the patient's work level by work level determination unit 320 (e.g., is the determined work level expected or within non-pathological limits based on the current activity?) and/or may be informative regarding excursions of the patient's work level from that expected based on the activity. The work level-activity correlation module 330 may provide information regarding acceptable work level deviations. In addition, a work-level correlation with activity level may be either a positive or negative correlation or may have a strong or weak association. Further, a work correlation evaluation with an activity level may show no correlative value (i.e., a zero correlation).

Figure 4:
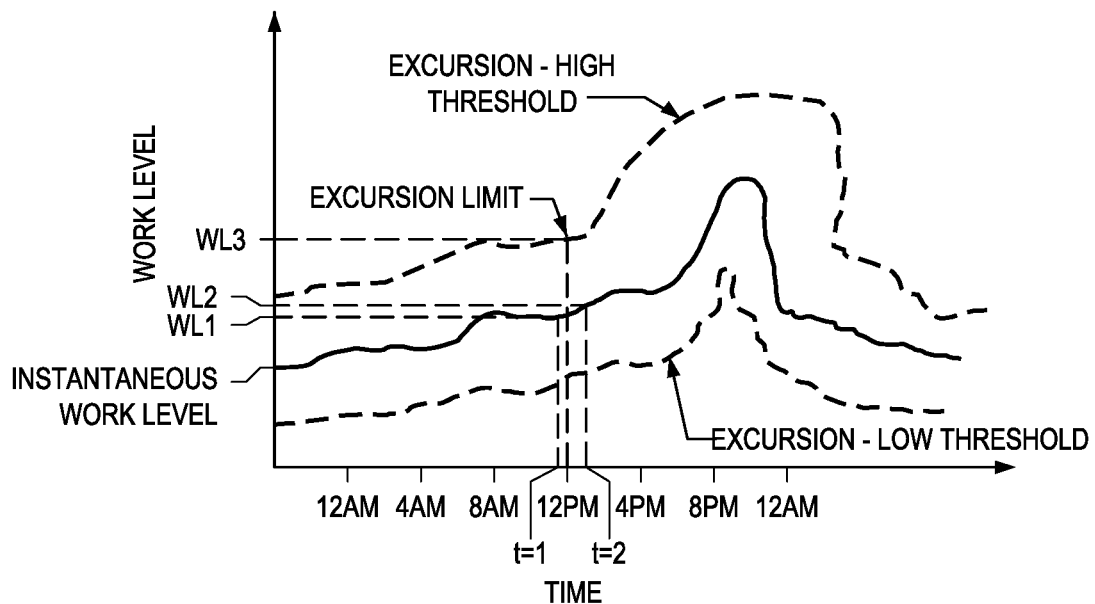
FIG. 4 shows a variation of work level range over the course of a day, according to some embodiments of the present disclosure.

The work level data module 150 may output one or more of work level data or acceptable work level deviation data commensurate with the activity level, among others. FIG. 4 shows a typical variation of work level over time of day for an exemplary patient. Generally, an instantaneous body work level (WL) may be at its lowest during sleep, moderate during most waking hours, and high during certain waking hours, e.g., during aerobic exercise, such as the hypothetical patient of FIG. 4 is performing at about 9 pm.

Figure 5:
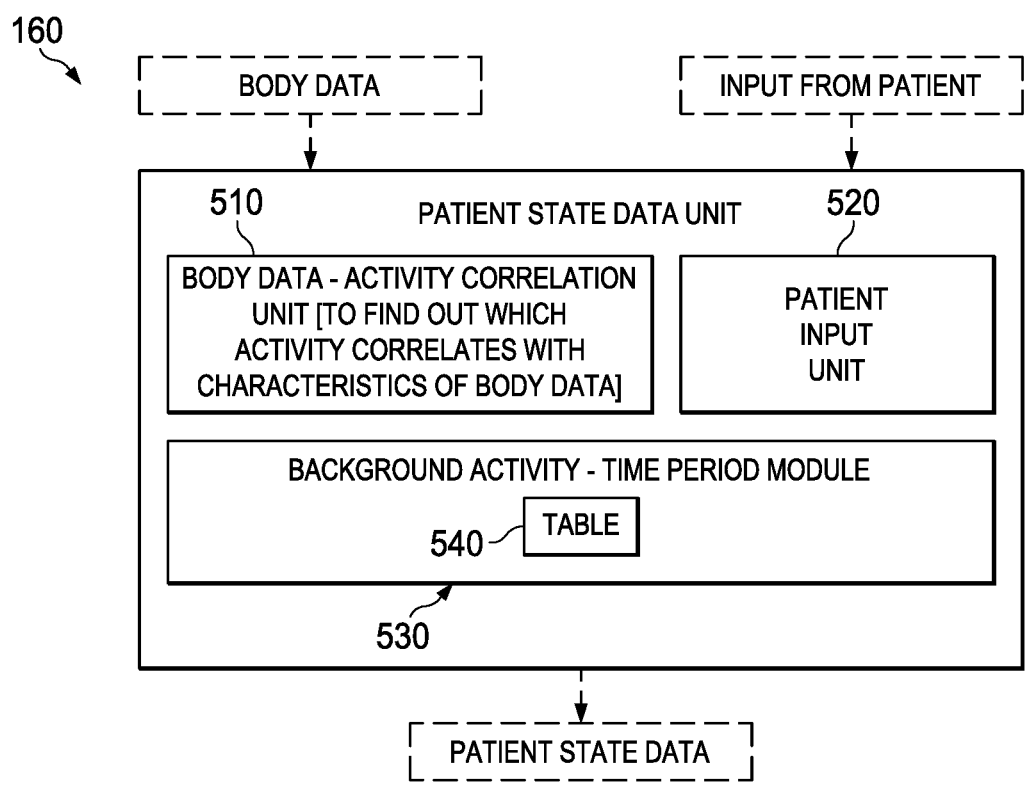
FIG. 5 shows a schematic diagram of a patient state data unit, according to some embodiments of the present disclosure.

As instantaneous work level increases, the thresholds for a work level excursion indicative of a partial or non-convulsive seizure may vary as well. The work level excursion may be a magnitude excursion, a rate of change excursion, or both. FIG. 5 shows a patient state data unit 160 in more detail. The patient state data unit 160 may receive body data and/or patient input (e.g., manual input). The patient state data unit 160 may comprise a body data—activity correlation unit 510 configured to find which activity may be correlated with which body data characteristics or properties. For example, if the body data is kinetic data and indicative of long, rhythmic strides (e.g., the patient is jogging or running) this activity may be correlated with certain heart rate, oxygen consumption or tidal respiratory volume data.

Generally, measurements of body work level may be useful for detection of epileptic convulsive seizures. Measurements of brain oxygen consumption may be useful for detection of both convulsive and partial seizures, for distinguishing between convulsive and partial seizures, and for distinguishing unilateral from bilateral partial seizures. A correlation or commensurateness of autonomic and/or other body signal with work level may also be useful to detect partial seizures.

The patient state data unit 160 may comprise a patient input unit 520 configured to receive patient manual input regarding the patient's activity or other parameters.

The patient state data unit 160 may comprise a background activity—time period module 530 configured to determine a background activity level at or over a given time period. The determination made by the background activity—time period module 530 may comprise looking up relevant background activity and/or time period data stored in a table 540. The background activity level may be useful for detection of both generalized and partial seizures using $O_2$ consumption given by arterio-venous differences in oxygen saturation measured at the appropriate anatomical sites.

In some situations, heart rate, heart rhythm, respiratory rate, respiratory rhythm/pattern, etc. may serve as proxies of activity level.

The patient state data unit 160 may output patient state data for use by other modules or units of the medical device 200.

Figure 6:
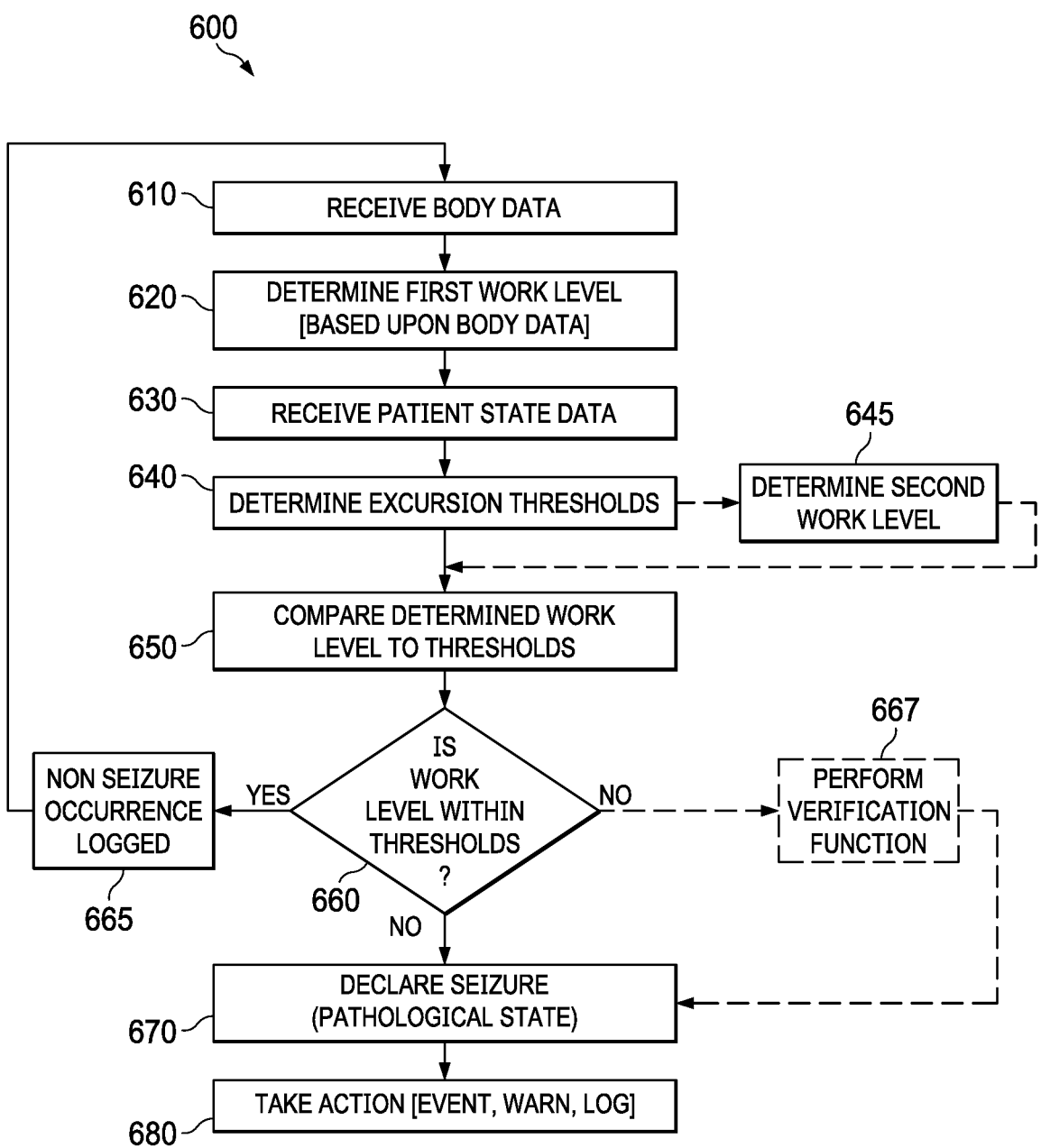
FIG. 6 shows a flowchart depiction of a method, according to some embodiments of the present disclosure.

FIG. 6 shows a flowchart representation of a method 600 according to some embodiments of the present disclosure. This method may be useful in detecting partial seizures from work level data. Body data, such as those types discussed supra, may be received at 610. A first work level may be determined at 620 based at least in part on the body data. Patient state data may be received at 630. In some embodiments, receiving patient state data at 630 is optional and need not be performed. In some situations, the patient state data may be inferred with high confidence, and without the need for receiving it, from the body data and/or other considerations. For example, if the patient has a very low activity level at a time between about midnight and 6:00 am, it may be inferred with high confidence that the patient is asleep.

Based at least in part on one or more of the received body data and the received patient state data, one or more work level excursions may be determined at 640. The work level excursion(s) may be relative to a threshold, outside a non-seizure range, or absolute (e.g., independent of a threshold or range). The non-seizure work level range may be defined at its lower bound by the patient's work level during stage 3 (slow-wave) sleep and at its upper bound by the patient's maximal volitional exertion (e.g., during intense exercise).

Similarly to and associated with the first work level determination at 620, a second work level may be determined at 645.

FIG. 7A shows one embodiment of determining a work level excursion threshold at 640 in more detail. A patient state may be determined at 710*a*, based on one or more of body data gathered from the patient, the time of day, the patient's activity history, the patient's current activity, and/or other factors. In light of the determined patient state, an expected work level may be determined at 760*a*. The expected work level may include statistical measures of central tendency, high percentile value, low percentile value, standard deviation, etc., relating to the expected work level.

From the expected work level, a work level threshold may be determined at 770*a*. The work level threshold may be determined from a percentile value based on the expected work level (e.g., the threshold may be set at the 95% ile or 99% ile of a statistical set of expected work level values) or a number-of-standard-deviations value based on the expected work level (e.g., the threshold may be set at 2 or 3 standard deviations above a measure of central tendency of expected work level). Regardless of how the threshold is set, the work level threshold may then be used in detecting seizures based on work level excursions above the threshold level.

FIG. 7B shows another embodiment of determining a work level excursion threshold at 640 in more detail. A patient state may be determined at 710, and a time of day may be determined at 720. This determination is generally not needed to establish an extreme work level excursion threshold, for reasons discussed supra. When activity patterns (by time of day and/activity type and level) exist, the work level corresponding to it with it may be determined at 730. It should be noted that the correlation between work level and activity pattern may be positive or negative, and strong or weak. If the patient state, activity level or type, is determined at 740 to deviate from a pattern or historical activity, then a maximum acceptable variation of work level based on the patient state, body data, and/or patient activity may be determined at 760. If the patient state or activity level or type do not deviate from a pattern or historical activity type or level as determined at 740, then it may be determined at 750 whether the work level pattern or patient state (e.g., asleep, resting awake, etc.) is commensurate (i.e., the observed values are similar to the expected values) with the patient's activity level. If the work level is commensurate with the patient's activity level, then flow may proceed to determining at 760 the maximum acceptable variation of work level, and determining the work level excursion threshold at 765. If the patient state is not commensurate with the patient's activity level, a seizure may be detected at 755 from this observation alone.

In one embodiment, the work level threshold is associated with an extreme work level, defined as that associated with body signals values at least 3 SD to the right of the mean of body signal values. In yet another embodiment, the occurrence of simple or complex partial seizures with motor manifestations either positive (e.g., muscle contractions) or negative (e.g., lack of movements/motionless) may be determined, based on the correlation of body signal values and work level.

Returning to FIG. 6, upon determination of at least the first work level at 620 and at least one work level excursion threshold at 640, the work level(s) may be compared at 650 to the threshold(s). If the work level is determined at 660 to be within the expected range or below a threshold(s), then a non-seizure occurrence may optionally be logged at 665 and flow may return to receiving at 610. A non-seizure occurrence may be further analyzed at a later time based upon additional data (i.e., the manual declaration of a seizure by the patient or the declaration of a seizure based upon a different declaration systems) to dynamically tune at least one work level excursion threshold.

If the work level is determined at 660 to exceed the work level excursion threshold(s), then a seizure or other pathological state may be declared at 670. If desired, a verification function, such as a confirmation test, may be performed at 667 prior to the declaration at 670. In either event, after declaration at 670, a further action, e.g., warning the patient, a caregiver, or a medical professional of the seizure or other pathological state; treating the pathological state; logging the pathological state's occurrence or a characteristic thereof; etc., may be performed at 680.

Figure 8:
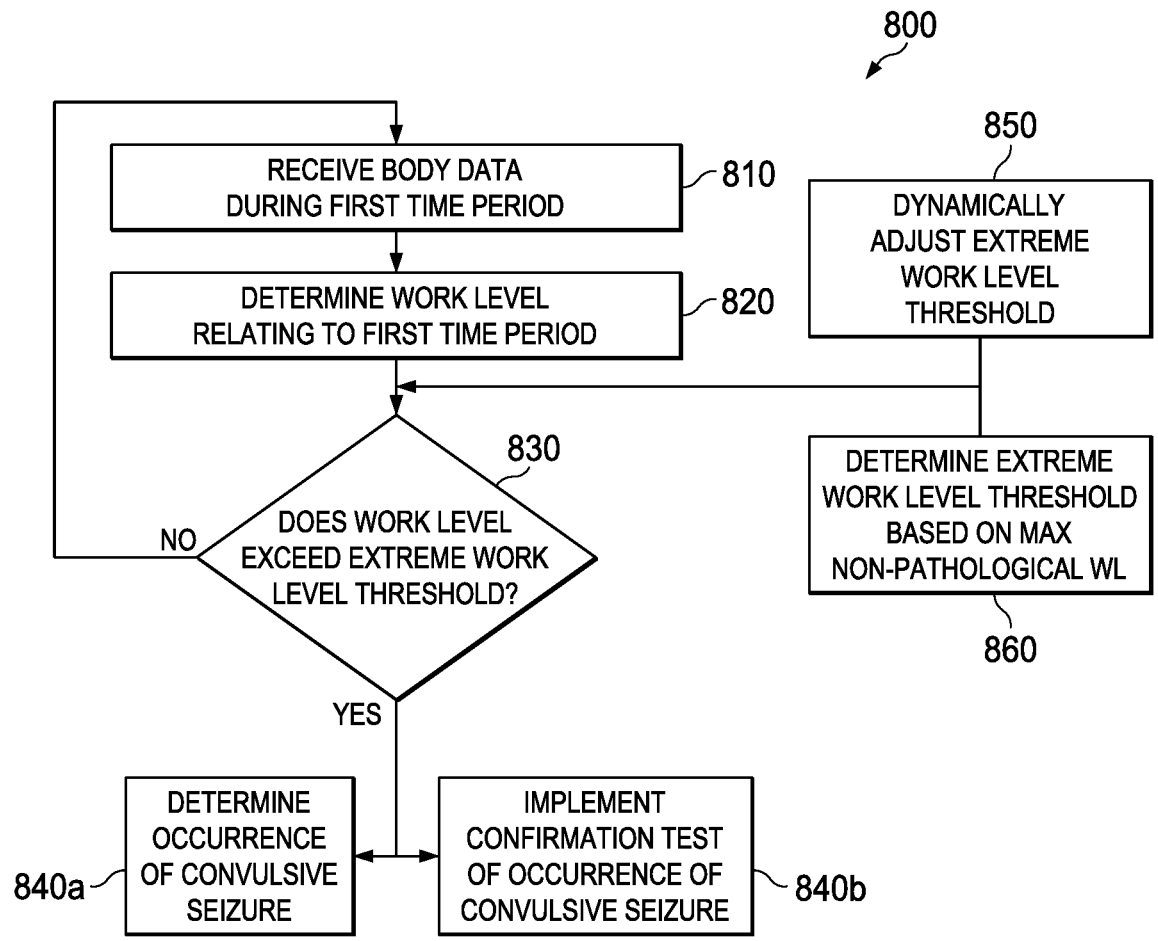
FIG. 8 shows a flowchart depiction of a method, according to some embodiments of the present disclosure.

FIG. 8 shows a flowchart representation of a method 800 of determining an occurrence of an epileptic convulsive seizure (e.g., a primarily or secondarily generalized tonic seizure, a tonic-clonic seizure, or a clonic-tonic-clonic seizure, among others) in a patient. The method 800 may comprise receiving at 810 body data from a patient during a first time period. The body data may comprise at least one of kinetic data, oxygen saturation data, blood pH data, oxygen consumption data, glucose consumption data, respiratory rate, tidal volume, or end tidal $CO_2$ data. Kinetic data includes, but is not limited to, force, duration of contraction, rate of movement, amplitude of movement, velocity of movement, direction of movement, and duration of movement. Kinetic or autonomic data may be used to determine a patient's activity level, and this activity level may be in turn used to determine ("by proxy") work level. Oxygen saturation data, blood pH data, oxygen consumption data, glucose consumption data, respiratory rate, tidal volume, end tidal $CO_2$ data, or the like may be used to determine work level.

A work level relating to said first time period may be determined at 820 based at least partially upon said body data. If the work level is determined at 830 to exceed an extreme work level threshold, then one or more responsive actions may be performed 840, such as determining at 840*a* the occurrence of a convulsive seizure, or implementing at 840*b* a confirmation test to confirm the occurrence of a convulsive seizure, delivering a therapy, issuing a warning of the occurrence of the seizure, logging the date and time of occurrence of the seizure, determining a response to said therapy, determining an adverse effect of said therapy, determining a severity of the seizure, or determining if the seizure resulted in an injury to the patient, among others.

The confirmation test implemented at 840*b* may be a test based on cardiac data of said patient, a test based on respiratory data of said patient, a test of the patient's body movements, a test of the patient's responsiveness, or a test of the patient's awareness. Alternatively or in addition, in one embodiment, the confirmation test may involve a determination whether the patient's work level is incommensurate with a range expected for the time of day, week, month, or year, whether the patient's work level is incommensurate with the patient's activity level, or both.

In some embodiments, if desired and/or appropriate, the extreme work level threshold may be dynamically adjusted at 850 based at least in part on one or more of a time of day, environmental conditions (e.g., time of day, ambient temperature, altitude, ambient humidity, etc.), a patient's body weight and height, a patient's body mass index, a patient's gender, a patient's age, an indicator of said patient's overall health, a patient's hydration status, or an indicator of said patient's overall fitness. For example, in a not-uncommon situation in the developing world, in a patient having a high fever under circumstances where the environmental temperature is also quite high, an intense complex partial seizure with a hypermotoric component may give rise to a detectable work level that, in cooler ambient conditions and/or for a non-febrile patient, would only be possible for a convulsive seizure. Alternatively or in addition, the extreme work level threshold may be determined at 860 based at least partially upon an historical indication of the patient's maximal non-pathological work level.

Figure 11:
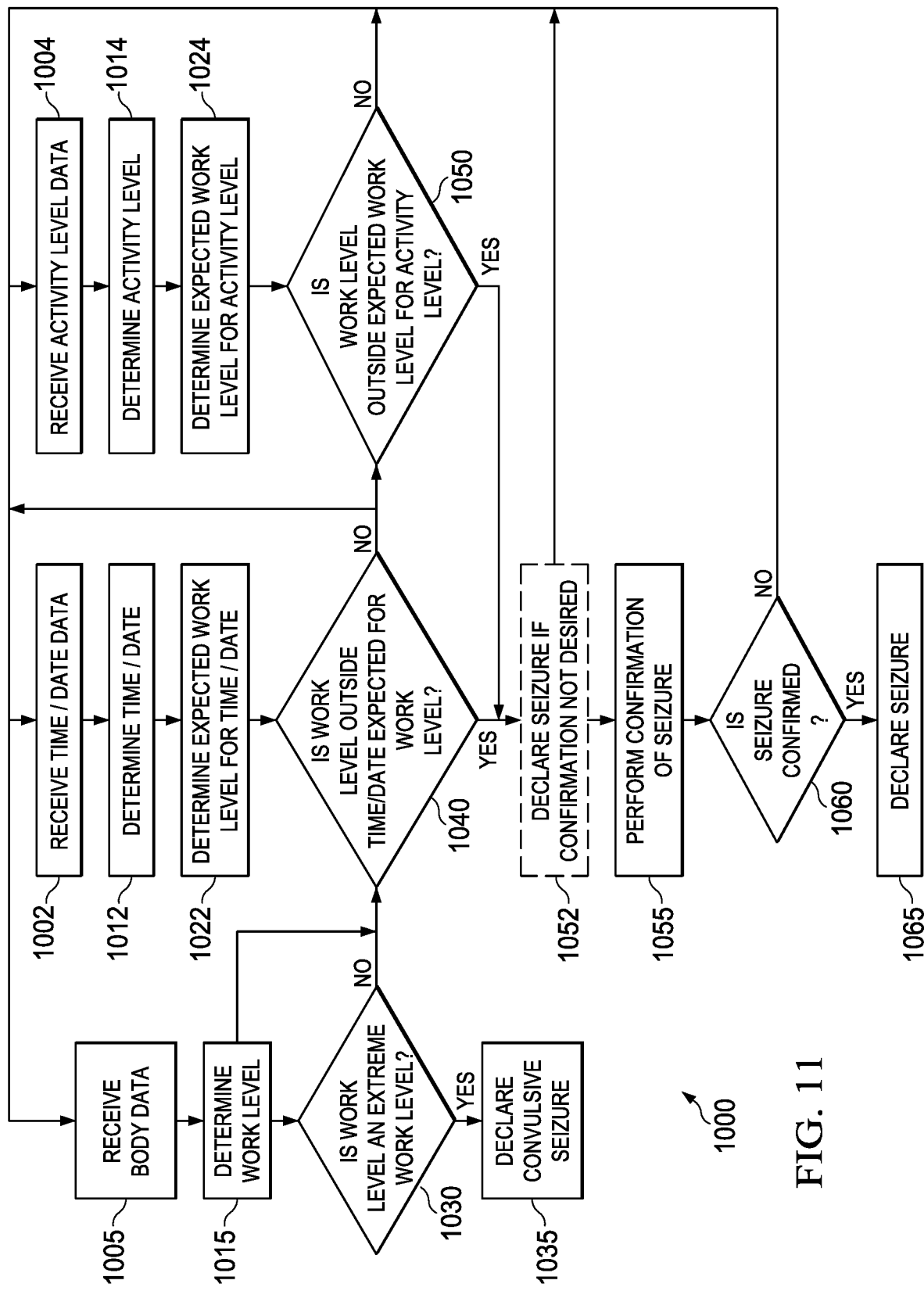
FIG. 11 shows a flowchart depiction of a method of detecting a seizure, according to some embodiments of the present disclosure.

Turning now to FIG. 11, this figure shows a method 1000 of detecting the occurrence of a seizure, according to some embodiments of the present disclosure. The method comprises at least receiving at 1005 body data relating to a patient's work level and determining at 1015 the patient's work level from the body data.

After determination at 1015 of the patient's work level, in one embodiment, it may be determined at 1030 whether the patient's work level is an extreme work level. If it is an extreme work level, a convulsive seizure may be declared at 1035. If it is not an extreme work level, flow may pass to either or both of determinations 1040 or 1050.

In other embodiments, after determination at 1015 of the patient's work level, flow may pass to either or both of determinations 1040 or 1050 and omit the determination at 1030.

In one embodiment, the method may comprise receiving at 1002 time/date data and determining at 1012 the time/date from the time/date data. In light of the time/date, an expected work level range may be determined at 1022. It may then be determined at 1040 if the work level (determined at 1015) is incommensurate with the work level range expected for the time/date. If it is incommensurate with the expected work level range, a seizure may be declared at 1052, if confirmation of the seizure is not desired, or a confirmation of the seizure may be performed at 1055.

For example, confirmation may be not desired if the therapy is safe, lacks side effects, and/or has not exceeded a maximum dosage in a current time window; if sensitivity, speed of detection, or both are desirable; if specificity is not particularly desirable; if the seizure has low intensity; or the like. For example, if a patient has partial seizures with secondary generalization (invariably associated with falls to the ground) that are abated if therapy is delivered within 5 sec of electrographic onset (while the patient is still aware and responsive), sensitivity and speed of detection may be maximized by omitting a confirmation of the declaration at 1052. Doing so may reduce the probability of serious injuries should the patient have a seizure.

On the other hand, confirmation may be desired if the therapy has unwelcome side effects; if specificity is desirable; if the drug supply (e.g., of a therapeutic drug administered automatically from a drug reservoir) or the battery life (e.g., of an electrical therapy device) is low. For example, if a patient with partial seizures with secondary generalization is lying in bed, and uses an anti-seizure therapy which is efficacious, but associated with intolerable side effects, specificity, not sensitivity or speed of detection, is paramount. Hence, a confirmation at 1055 of the seizure may be desirable. In one embodiment, the method may comprise receiving at 1004 activity level data regarding the patient and determining the patient's activity level at 1014. In light of the patient's activity level, an expected work level range may be determined at 1024. It may then be determined at 1050 if the work level (determined at 1015) is incommensurate with the work level range expected for the patient's activity level. If it is incommensurate with the expected work level range, a seizure may be declared at 1052, if confirmation is not desired, or a confirmation of a seizure may be performed at 1055. More specifically, if said observed work level is incommensurate with the activity level at the time of the measurement, but is within the physiological range, the epileptic seizure may be classified as partial and if the work level is above the upper range for non-ictal/physiological activity (e.g., it reaches or is above the extreme threshold) the seizure may be classified as epileptic convulsive.

A confirmation of a seizure may be performed at 1055 using techniques described elsewhere herein, described in other patents or applications to Cyberonics, Inc., or Flint Hills Scientific, LLC incorporated by reference herein, or known to the person of ordinary skill in the art having the benefit of the present disclosure. After performing a confirmation at 1055, if it is determined at 1060 that a seizure is confirmed, a seizure may be declared at 1065, if the extreme work level has not been reached or exceed and if the work level is not commensurate with the activity level.

If a seizure is declared at 1052, or it is determined at 1060 that a seizure is not confirmed, then flow may return to receiving body data at 1005, receiving time/date data at 1002, and/or receiving activity level data at 1004. Flow may also return to one or more of elements 1005, 1002, or 1004 upon a "NO" result for the determinations at 1030, 1040, and/or 1050.

Figure 9A:
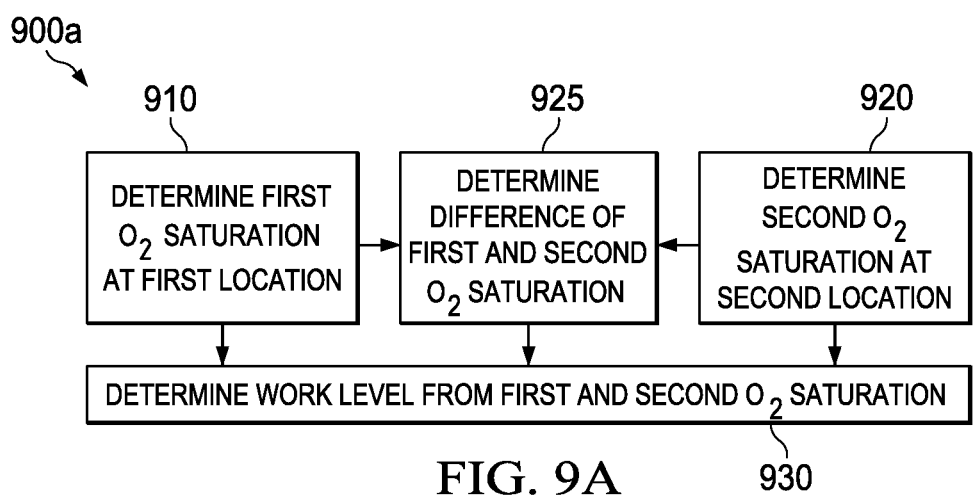
FIG. 9A shows a flowchart depiction of a method of measuring the work level of the patient's body or a part thereof, according to some embodiments of the present disclosure.

Turning now to FIG. 9A, this figure shows a method 900a of determining a work level of a subject's body or a part thereof, which may be as follows. The method may comprise determining at 910 a first oxygen saturation, concentration, or pressure of the subject's blood at a first location. The method may comprise determining at 920 a second oxygen saturation, concentration, or pressure of the subject's blood at a second location. In some embodiments, the method may comprise determining at 925 a difference or a ratio between the first oxygen saturation, concentration, or pressure and the second oxygen saturation, concentration, or pressure. A difference determined at 925 can be determined simply by subtracting the second oxygen saturation, concentration, or pressure from the first, or vice versa and also encompasses determining the absolute value of the result of subtraction, should the result of subtraction be negative. A ratio determined at 925 can be determined simply by dividing the second oxygen saturation, concentration, or pressure by the first, or vice versa. The method may comprise determining at 930 the work level of the subject's body or part thereof based on the first and second oxygen saturation, concentration, or pressures and/or the difference between them.

In some embodiments, the first location is in a carotid artery; the second location is in a jugular vein; and the body part is the patient's brain. The first location and the second location may be located on a first side of the patient's body. This embodiment may be useful for detection of partial seizures, by measuring energy consumption of the brain. In other words, in some embodiments, the difference in oxygen saturation, concentration, or pressure between a carotid artery and an ipsilateral jugular vein may be used to detect the occurrence of partial seizures in patient with epilepsy.

It should be noted that, although the description so far has focused on gathering oxygen information of the anterior (e.g., carotid) circulation, the person of ordinary skill in the art would understand that the same method and procedure could be applied to the posterior circulation (vertebral arteries and branches thereof and posterior venous sinuses) to yield other information useful in determining a work level for the patient's brain, one or more parts thereof, the patient's body, or one or more parts thereof.

Figure 9B:
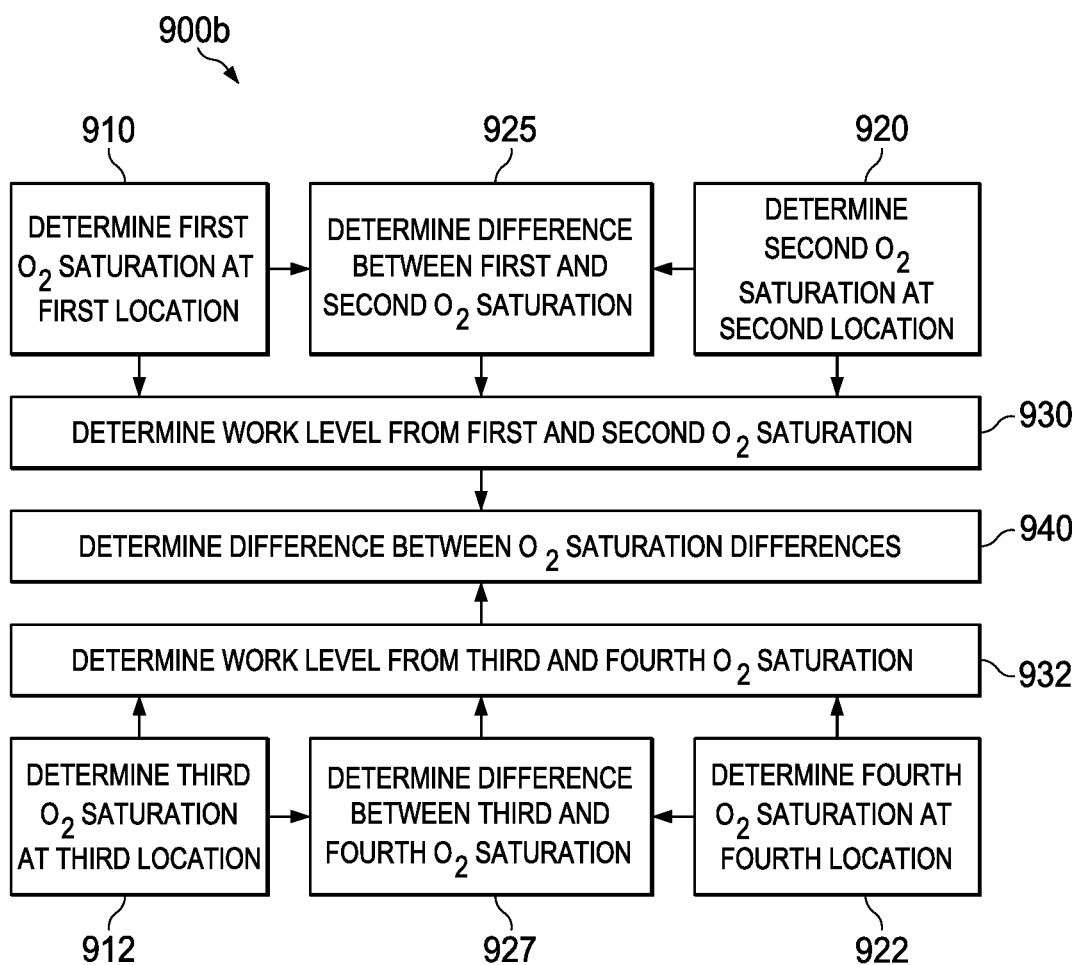
FIG. 9B shows a flowchart depiction of a method of measuring the work level of the patient's body or a part thereof, according to some embodiments of the present disclosure.

Turning to FIG. 9B, which depicts a method 900b which has many like elements with FIG. 9A that will not be further described, some embodiments may comprise one or more of determining at 912 a third oxygen saturation, concentration, or pressure of the subject's blood at a third location, determining at 922 a fourth oxygen saturation, concentration, or pressure of the subject's blood at a fourth location, determining at 927 a difference between the third oxygen saturation, concentration, or pressure and the fourth oxygen saturation, concentration, or pressure, or determining at 932 the work level of the subject's body or part thereof based on the third and fourth oxygen saturation, concentration, or pressures and/or the difference between them.

Thus, in some embodiments, the method 900b may comprise determining the work level of at least two regions of the subject's brain. In one embodiment, the at least two regions are the left and right hemispheres of the brain. In other embodiments, two or more of the at least two regions may be within the same hemisphere. The work level of the at least two regions of the subject's brain may be determined simultaneously, may be determined for overlapping time periods, or may be determined for non-overlapping time periods.

In embodiments comprising simultaneous bilateral measurements of oxygen consumption (e.g., the left carotid artery may be the first location, the left jugular vein may be the second location, the right carotid artery may be the third location, and the right jugular vein may be the fourth location), such bilateral measurements may provide information regarding the unilaterality or bilaterality of seizures, the side of seizure origin, and the time of spread (if any) to the contralateral brain region. Bilateral measurements may also help distinguish partial from generalized and for the latter, primarily v. secondarily generalized. For seizures associated with movements of most or all body parts, oxygen consumption measurements may help distinguish epileptic from non-epileptic (psychogenic, "pseudo-seizures") seizures. Measurements of oxygen consumption of certain brain regions (e.g., occipital lobes) not supplied by the carotid system, may be performed from posterior circulation system.

In some embodiments, the first location is in a blood vessel selected from a left ventricle, an aorta, a branch of the aorta (e.g., carotid artery), or a sub-branch of the aorta (e.g., middle cerebral artery); the second location is in a superior vena cava, an inferior vena cava, a right ventricle, a pulmonary artery, a jugular vein or a cerebral venous sinus; and the work level is determined of the subject's body.

In other embodiments the difference in oxygen saturation, concentration, or pressure between systemic or body arterial blood (which may be measured, for example, in the left ventricle) and systemic or body venous blood (which may be measured, for example, in the right ventricle) may be used to determine if the patient had an epileptic convulsion.

In some embodiments, information regarding work level may be determined by use of a single oxygen saturation, concentration, or pressure measurement at a single location, if compared to an appropriate control. In one embodiment, the oxygen saturation, concentration, or pressure measured at the first location may be compared with a negative control, i.e., an oxygen saturation, concentration, or pressure measured at the first location during a verified non-seizure state. In another embodiment, the oxygen saturation, concentration, or pressure measured at the first location may be compared with a positive control, i.e., an oxygen saturation, concentration, or pressure measured at the first location during a verified seizure state, such as partial seizure or a convulsive seizure. This embodiment may allow determinations of work level by use of only one oxygen saturation, concentration, or pressure sensor.

In yet another embodiment, a difference in the difference in arterial and venous blood oxygen saturation, concentration, or pressure as measured in a carotid artery and jugular vein compared to that measured in a right and left ventricles may be used to determine if the patient had a convulsion or a partial seizure.

In yet another embodiment, a bilateral difference between (i) the difference in oxygen saturation, concentration, or pressure measured in the left carotid artery and the left jugular vein and (ii) the difference in oxygen saturation, concentration, or pressure measured in the right carotid artery and the right jugular vein may be used to determine if the patient had a unilateral or a bilateral partial seizure. In other words, the difference between the oxygen saturation, concentration, or pressure differences may be determined (e.g., at FIG. 9B, 940). This embodiment may be particularly useful regarding seizures having an origin in the mesiotemporal lobe.

The methods depicted in FIGS. 6-9 and 11 and/or described above may be governed by instructions that are stored in a non-transitory computer readable storage medium and that are executed by, e.g., a processor 217 of the medical device 200. Each of the operations shown in FIGS. 6-9 and 11 and/or described above may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

In some embodiments, the present disclosure relates to one or more of the following numbered paragraphs:

101. A non-transitory computer readable program storage unit encoded with instructions that, when executed by a computer, perform a method of determining an occurrence of an epileptic seizure in a patient, comprising:
receiving body data from a patient during a first time period,
determining a work level relating to said first time period at least based partially upon said body data;
determining an activity level of said patient during said first time period;
determining whether said work level is incommensurate with said activity level; and
determining said occurrence of said epileptic seizure, based at least in part on said incommensurateness of said work level with said activity level.

102. The non-transitory computer readable program storage unit of numbered paragraph 101, further comprising: determining if said incommensurate work level reaches or exceeds an extreme work level, classifying said epileptic seizure as partial if said incommensurate work level does not reach or exceed an extreme work level threshold and classifying said seizure as convulsive if said work level reaches or exceeds an extreme work level threshold.

103. The non-transitory computer readable program storage unit of numbered paragraph 101, further comprising implementing a confirmation test of said epileptic seizure in response to said work level being incommensurate with said activity level, and confirming said occurrence of said epileptic seizure based at least in part on a result of said confirmation test.

104. The non-transitory computer readable program storage unit of numbered paragraph 101, wherein determining said activity level comprises:
determining at least one environmental condition selected from time of day, temperature, humidity, or altitude;
and receiving patient body data relating to at least one of current kinetic activity, current cognitive activity, or current emotional activity.

105. The non-transitory computer readable program storage unit of numbered paragraph 101, wherein determining whether said work level is incommensurate with said activity level comprises:
determining an expected work level based on the activity level; and
comparing said work level and said expected work level.

106. The non-transitory computer readable program storage unit of numbered paragraph 105, wherein determining said expected work level is based at least in part on at least one of a patient state, said patient's body weight and height, said patient's body mass index, said patient's gender, said patient's age, said patient's hydration status, an indicator of said patient's overall health, an indicator of said patient's overall fitness, or a determination that said patient state relating to said time of day corresponds with a patient's historical activity.

107. The non-transitory computer readable program storage unit of numbered paragraph 106, wherein determining said patient state comprises performing at least one of:
receiving a patient body data indicative of said patient state; or
performing a correlation between said body data and at least one of a plurality of candidate states, and selecting at least one of said candidate states as the patient state based upon said correlation.

108. The non-transitory computer readable program storage unit of numbered paragraph 107, wherein performing said correlation between said body data and at least one of said plurality of candidate state comprises performing a lookup of said plurality of candidates based upon said body data.

109. The non-transitory computer readable program storage unit of numbered paragraph 101, further comprising confirming said occurrence is based on at least one of: a work level incommensurate with a work level range expected for the patient at the time of day, week, month, season, or year of occurrence, level of activity or said work level exceeding an extreme work level at the time of occurrence.

110. The non-transitory computer readable program storage unit of numbered paragraph 109, wherein initiating said confirming comprises examining at least one of a cardiac data, a respiratory data, an oxygen saturation data, a metabolic data, or an endocrine data to confirm said pathological state.

111. The non-transitory computer readable program storage unit of numbered paragraph 110, wherein said body data comprises at least one of kinetic data, oxygen saturation data, blood pH data, oxygen consumption data, glucose consumption data, respiratory rate, tidal volume, or end tidal $CO_2$ data.

112. The non-transitory computer readable program storage unit of numbered paragraph 101, further comprising determining a non-seizure work level range, wherein said non-seizure work level range is based at least in part on one or more of a time of day, environmental conditions, a patient's body weight and height, said patient's body mass index, said patient's gender, said patient's age, said patient's hydration status, an indicator of said patient's overall health, or an indicator of said patient's overall fitness.

113. The non-transitory computer readable program storage unit of numbered paragraph 109, wherein said confirmation test is selected from a test based on cardiac data of said patient, a test based on respiratory data of said patient, a test of the patient's body movements, a test of the patient's responsiveness, or a test of the patient's awareness.

201. A non-transitory computer readable program storage unit encoded with instructions that, when executed by a computer, perform a method of determining an occurrence of an epileptic seizure in a patient during a first time period, comprising:
determining a work level relating to said first time period;
determining an expected work level range during said first time period;
determining whether said work level is incommensurate with said expected work level range during said first time period; and
determining said occurrence of said epileptic seizure, based at least in part on said work level being incommensurate with said expected work level range during said first time period.

202. The non-transitory computer readable program storage unit of numbered paragraph 201, further comprising implementing a confirmation test of said epileptic seizure in response to said work level being incommensurate with said expected work level range, and wherein determining said occurrence of said epileptic seizure is based at least in part on a result of said confirmation test.

203. The non-transitory computer readable program storage unit of numbered paragraph 201, wherein determining said expected work level range is based at least in part on a time of day, week, month, season, or year comprised by said first time period.

204. The non-transitory computer readable program storage unit of numbered paragraph 201, further comprising confirming said occurrence is based on at least one of: said work level exceeding an extreme work level at the time of occurrence; or a work level incommensurate with a work level range expected for the patient based on the patient's activity level at the time of occurrence.

205. The non-transitory computer readable program storage unit of numbered paragraph 202, wherein said confirmation test is selected from a test based on cardiac data of said patient, a test based on respiratory data of said patient, a test of the patient's body movements, a test of the patient's responsiveness, or a test of the patient's awareness.

301. A non-transitory computer readable program storage unit encoded with instructions that, when executed by a computer, perform a method of determining an occurrence of an epileptic seizure in a patient, comprising at least two of:
determining a work level incommensurate with a work level range expected for the patient at least one temporal occurrence at one of a time of day, week, month, season, or year of occurrence;
determining a work level exceeding an extreme work level at a time of occurrence of said epileptic seizure; or
determining a work level incommensurate with the patient's activity level at the time of occurrence.

401. A non-transitory computer readable program storage unit encoded with instructions that, when executed by a computer, perform a method of classifying a seizure in a patient, comprising at least one of:
determining a seizure to be an epileptic seizure based on determining at least one of:
a work level incommensurate with a work level range expected for the patient for at least one temporal window from one of a time of day, week, month, season, or year of occurrence;
a work level exceeding an extreme work level at a time of occurrence of said seizure; or
a work level incommensurate with the patient's activity level at the time of occurrence; or
determining an epileptic seizure to be a convulsive seizure based on determining a work level exceeding an extreme work level at a time of occurrence of said seizure, or a determining an epileptic seizure to be non-convulsive based on the work level during said seizure being incommensurate with the patient's activity level at the time of occurrence, but not exceeding an extreme work level threshold.

501. A non-transitory computer readable program storage unit encoded with instructions that, when executed by a computer, perform a method of determining an occurrence of an epileptic convulsive seizure in a patient, comprising:
receiving body data from a patient during a first time period;
determining a work level relating to said first time period at least based partially upon said body data;
determining whether said work level exceeds an extreme work level threshold;

performing a responsive action, in response to a determination that said work level exceeds said extreme work level threshold, wherein said responsive action is selected from:
determining said occurrence of said convulsive seizure, or
implementing a confirmation test to confirm said occurrence of said convulsive seizure.

502. The non-transitory computer readable program storage unit of numbered paragraph 501, wherein said body data comprises at least one of kinetic data, oxygen saturation data, blood pH data, oxygen consumption data, glucose consumption data, or end tidal $CO_2$ data 503. The non-transitory computer readable program storage unit of numbered paragraph 501, wherein said confirmation for said occurrence is selected from a test based on cardiac data of said patient, a test based on respiratory data of said patient, a test of the patient's body movements, a test of the patient's responsiveness, or a test of the patient's awareness.

504. The non-transitory computer readable program storage unit of numbered paragraph 501, further comprising dynamically adjusting said extreme work level threshold, based at least in part on one or more of a time of day, environmental conditions, a patient's body weight and height, said patient's body mass index, said patient's gender, said patient's age, said patient's hydration status, an indicator of said patient's overall health, or an indicator of said patient's overall fitness.

505. The non-transitory computer readable program storage unit of numbered paragraph 501, wherein determining said extreme work level threshold comprises determining said extreme work level threshold based at least partially upon an historical indication of the patient's maximal non-pathological work level.

506. A medical device system, comprising:
at least one sensor, each configured to collect at least one body signal from a patient relating to a work level of said patient; and
a medical device, comprising:
a body data module configured to receive body data;
a patient state data unit configured to determine the patient state based upon said body data;
a work level data module configured to determine a patient's first work level during a first time period, and the patient's second work level during a second time period;
a work level excursion module configured to determine a work level excursion threshold based at least one said body data, time of day, or said patient state; and
a work level excursion test module configured to determine whether said second work level exceeds said first work level greater by than an amount of said first work level excursion threshold; and
a controller to perform at least one of warning of a pathological state, providing a therapy, or logging said occurrence of said pathological state.

507. The medical device system of numbered paragraph 506, wherein said medical device is configured to perform a test based on cardiac data of said patient, a test based on kinetic data of said patient, a test of the patient's responsiveness, or a test of the patient's awareness to confirm said pathological state.

508. The medical device system of numbered paragraph 506, wherein said non-pathological work level range module is configured to determine a non-pathological work level range of said patient, further based at least in part on one or more of a time of day, an indicator of said patient's overall health, an indicator of said patient's overall fitness, a patient's body weight and height, a patient's body mass index, a patient's gender, or a patient's age.

509. The medical device system of numbered paragraph 506, wherein said work level data module comprises:
a body data analysis module to determine a value relating to at least one of a cardiac data, blood pressure data, respiration data, blood gas data, patient kinetic data, responsiveness data, endocrine data, metabolic data, or tissue stress marker data; and
a work level determination unit to determine said first and second patient work levels based upon at least one of said cardiac data, blood pressure data, respiration data, blood gas data, patient kinetic data, responsiveness data, endocrine data, metabolic data, or tissue stress marker data.

510. The medical device system of numbered paragraph 506, wherein said patient state module comprises:
a background activity time period module configured to provide data relating to historic patient activity in relation to time of day;
a body data activity correlation unit configured to correlate said body data to at least one of a plurality of candidate states based upon said data relating to historic patient activity; and
a patient input unit configured to receive and input from said patient.

511. The medical device system of numbered paragraph 506, further comprising:
a warning unit to provide a warning in response to a determine that a pathological state has occurred;
a therapy unit configured to provide a therapy in response to a determine that a pathological state has occurred; and
a logging unit to log an occurrence of said pathological state.

512. The medical device system of numbered paragraph 506, wherein said at least one sensor comprises at least one of:
an autonomic data acquisition unit configured to acquire at least one of heart beat data, blood pressure data, respiration data, or blood gas data;
a neurological data acquisition unit configured to acquire kinetic data selected from the group consisting of accelerometer data and inclinometer data.
an endocrine data acquisition unit configured to acquire endocrine data,
a metabolic data acquisition unit configured to acquire metabolic data;
a tissue stress marker data acquisition unit configured to acquire tissue stress marker data;
a physical fitness data acquisition unit configured to acquire data relating to the patient's physical fitness; or
an environmental conditions sensor configured to acquire data relating to at least one of time of day, ambient temperature, altitude, ambient humidity, barometric pressure, or luminance.

513. A medical device, comprising:
a body data module configured to receive body data;
a patient state data configured to determine the patient state based upon said body data;
a work level data module configured to determine a first patient work level during a first time period, and a second patient work level during a second time period;
a work level excursion module configured to determine a work level excursion threshold based at least one said body data, time of day, or said patient state; and
a work level excursion test module configured to determine whether said second work level exceeds said first work level by at least said first work level excursion threshold; and a controller to perform at least one of warning of a pathological state, providing a therapy, or logging said pathological state, in response to a determination that said second work level exceeds said first work level greater by than an amount of said first work level excursion threshold.

514. The medical device of numbered paragraph 513, further comprising:
a warning unit to provide a warning in response to a determine that a pathological state has occurred;
a therapy unit configured to provide a therapy in response to a determine that a pathological state has occurred; and
a logging unit to log an occurrence of said pathological state.

515. The medical device system of numbered paragraph 513, wherein said pathological state is an epileptic event.

516. A non-transitory computer readable program storage unit encoded with instructions that, when executed by a computer, perform a method of determining a work level of a subject's brain, comprising:
determining a first oxygen saturation of the subject's blood at a first location in a carotid artery;
determining a second oxygen saturation of the subject's blood at a second location in a jugular vein;
determining a difference between the first oxygen saturation and the second oxygen saturation; and
determining the work level of the subject's brain based on the difference.

517. A medical device system, comprising:
a first sensor configured to collect first oxygen saturation data of a subject's blood from a first location in a carotid artery;
a second sensor configured to collect second oxygen saturation data of the subject's blood from a second location in a jugular vein; and
a medical device, comprising:
a first location oxygen saturation module configured to determine a first oxygen saturation from said first oxygen saturation data;
a second location oxygen saturation module configured to determine a second oxygen saturation from said second oxygen saturation data;
an oxygen saturation difference module configured to determine a difference between the first oxygen saturation and the second oxygen saturation; and
a brain work level determination module configured to determine a work level of the subject's brain based on the difference.

518. A non-transitory computer readable program storage unit encoded with instructions that, when executed by a computer, perform a method of determining a work level of a subject's body, comprising:
determining a first oxygen saturation of the subject's blood at a first location in a blood vessel selected from a left ventricle of a heart;
determining a second oxygen saturation of the subject's blood at a second location in a right ventricle of a heart;
determining a difference between the first oxygen saturation and the second oxygen saturation; and
determining the work level of the subject's body based on the difference.

519. A medical device system, comprising:
a first sensor configured to collect oxygen saturation data of a subject's blood from a first location selected from at least one of an ascending aorta or a left ventricle;
a second sensor configured to collect second oxygen saturation data of the subject's blood from a second location in an inferior vena cava; and
a medical device, comprising:
at least one oxygen saturation modules configured to determine oxygen saturation from said first sensor and said second sensor;
an oxygen saturation difference module configured to determine an oxygen saturation difference between said first sensor and said second sensor; and
a seizure classification module to classify a seizure as one of a non-epileptic seizure, a convulsive epileptic seizure or a non-convulsive epileptic seizure based upon said output from said oxygen saturation module.

520. The medical device system of numbered paragraph 506, wherein said patient state module determines a patient state based upon body data.

601. A non-transitory computer readable program storage unit encoded with instructions that, when executed by a computer, perform a method of determining a work level of a subject's body or a part thereof, comprising:
determining a first oxygen saturation, concentration, or pressure of the subject's blood at a first location in a blood vessel selected from a left ventricle, an aorta, a branch of the aorta, or a sub-branch of the aorta;
determining a second oxygen saturation, concentration, or pressure of the subject's blood at a second location in a superior vena cava, an inferior vena cava, a right ventricle, or a pulmonary artery; and
determining the work level of the subject's body or the part thereof based on the first oxygen saturation, concentration, or pressure and the second oxygen saturation, concentration, or pressure.

602. The non-transitory computer readable program storage unit of numbered paragraph 601, wherein the method further comprises determining a difference or a ratio between the first oxygen saturation, concentration, or pressure and the second oxygen saturation, concentration, or pressure.

603. A medical device system, comprising:
a first sensor configured to collect first oxygen saturation, concentration, or pressure data of a subject's blood from a first location in a blood vessel selected from a left ventricle, an aorta, a branch of the aorta, or a sub-branch of the aorta;
a second sensor configured to collect second oxygen saturation, concentration, or pressure data of the subject's blood from a second location in a superior vena cava, an inferior vena cava, a right ventricle or a pulmonary artery; and
a medical device, comprising:
a first location oxygen saturation, concentration, or pressure module configured to determine a first oxygen saturation, concentration, or pressure from said first oxygen saturation, concentration, or pressure data;
a second location oxygen saturation, concentration, or pressure module configured to determine a second oxygen saturation, concentration, or pressure from said second oxygen saturation, concentration, or pressure data; and
a brain work level determination module configured to determine a work level of the subject's body based on the first oxygen saturation, concentration, or pressure and the second oxygen saturation, concentration, or pressure.

604. The medical device system of numbered paragraph 603, wherein the medical device further comprises
an oxygen saturation, concentration, or pressure difference module configured to determine a difference or a ratio between the first oxygen saturation, concentration, or pressure and the second oxygen saturation, concentration, or pressure.

701. A method of determining a work level of a patient's body or a part thereof, comprising:
determining at least one cardiac signal from said patient; and
determining said work level, based on said at least one cardiac signal.

702. The method of claim 701, wherein the at least one cardiac signal is a heart rate of said patient.

What is claimed:

1. A medical device, comprising:
at least one sensor configured to collect at least one body signal from a patient;
one or more processors configured to determine a first patient state based on the at least one body signal from the patient received from the at least one sensor, the one or more processors are configured to determine a first time of day determination, wherein the one or more processors are configured to generate a non-seizure state based on the first time of day determination and the first patient state.

2. The medical device of claim 1, wherein the one or more processors are configured to determine a second time of day determination and to generate a seizure state based on the second time of day determination and the first patient state.

3. The medical device of claim 1, wherein the one or more processors are configured to determine a patient's activity history, the one or more processors are configured to determine a second time of day determination and to generate a seizure state based on the second time of day determination and the patient's activity history.

4. The medical device of claim 1, wherein the one or more processors are configured to determine a patient's activity history, the one or more processors are configured to determine a second time of day determination and to generate a non-seizure state based on the second time of day determination and the patient's activity history.

5. The medical device of claim 4, wherein the one or more processors are configured to determine a third time of day determination and to generate the seizure state based on the third time of day determination and the patient's activity history.

6. The medical device of claim 1, wherein the first patient state is based on a work level determination.

7. The medical device of claim 6, wherein the work level determination is based on a magnitude excursion function.

8. The medical device of claim 6, wherein the work level determination is based on a rate of change excursion function.

9. The medical device of claim 1, further comprising an environmental monitor configured to receive environmental data, wherein the one or more processors are configured to determine at least one of the non-seizure state and a seizure state based on the first patient state, the first time of day determination, and the environmental data.

10. A method implemented via a medical device, comprising:
collecting via one or more processors of the medical device, at least one body signal from a patient;
determining via the one or more processors of the medical device a first patient state based on the at least one body signal collected from the patient; determining via the one or more processors of the medical device a first time of day determination;
and generating via the one or more processors of the medical device a non-seizure state based on the first time of day determination and the first patient state.

11. The method of claim 10, further comprising generating via the one or more processors of the medical device a seizure state based on second time of day determination and a first patient state.

12. The method of claim 10, further comprising determining via the one or more processors of the medical device a patient's activity history and generating the non-seizure state when a second time of day determination is generated based on the patient's activity history.

13. The method of claim 10, further comprising determine via the one or more processors of the medical device a patient's activity history and generating a seizure state when a second time of day determination is generated based on the patient's activity history.

14. The method of claim 13, further comprising generating via the one or more processors of the medical device the seizure state when a third time of day determination is generated based on the patient's activity history.

15. The method of claim 10, wherein the first patient state is based on a work level determination.

16. The method of claim 15, wherein the work level determination is based on a magnitude excursion function.

17. The method of claim 15, wherein the work level determination is based on a rate of change excursion function.

18. The method of claim 10, further comprising receiving via the one or more processors of the medical device environmental data and determining at least one of the non-seizure state and a seizure state based on the first patient state, the time of day, and the environmental data.

19. A medical system, comprising:
at least one sensor on one or more medical devices configured to collect at least one body signal from a patient;
one or more processors configured to determine a first patient state based on the at least one body signal from the patient received from the at least one sensor, the one or more processors are configured to determine a time of day, wherein the one or more processors are configured to generate a non-seizure state when a first time of day determination is generated, wherein the one or more processors are configured to generate a seizure state when a second time of day determination is generated.

20. The medical system of claim 19, wherein the one or more processors are configured to determine a patient's activity history, the one or more processors are configured to generate the non-seizure state when the second time of day determination is generated based on a first patient's activity history data, the one or more processors are configured to generate the seizure state when the second time of day determination is generated based on a second patient's activity history data, the one or more processors are configured to generate the seizure state when a third time of day determination is generated based on a third patient's activity history data.

* * * * *